United States Patent [19]

Flick et al.

[11] 4,224,234

[45] Sep. 23, 1980

[54] METHOD FOR PREPARATION OF ORTHOSILICIC ACID TETRAALKYL ESTERS

[75] Inventors: Wilhelm Flick, Cologne; Hermann Richtzenhain, Much-Schwellenbach; Volker Hunger; Wilhelm Joch, both of Niederkassel, all of Fed. Rep. of Germany

[73] Assignee: Dynamit Nobel Aktiengesellschaft, Troisdorf, Fed. Rep. of Germany

[21] Appl. No.: 30,499

[22] Filed: Apr. 16, 1979

[30] Foreign Application Priority Data

Apr. 15, 1978 [DE] Fed. Rep. of Germany ....... 2816386

[51] Int. Cl.$^2$ ............................................. C07F 7/04
[52] U.S. Cl. ................................. 556/472; 556/483

[58] Field of Search .................................. 260/448.8 A

[56] References Cited

U.S. PATENT DOCUMENTS 3,627,807   12/1971   Bleh et al. ...................... 260/448.8 A Primary Examiner—Paul F. Shaver
Attorney, Agent, or Firm—Sprung, Felfe, Horn, Lynch & Kramer

[57] ABSTRACT

An improvement in the preparation of orthosilicic acid tetraalkyl esters by reaction of metallic silicon with alcohol in the presence of alkali alcoholate is disclosed, the improvement residing in carrying out the reaction in the co-presence of an ether alcohol or alkanolamine as cocatalyst.

6 Claims, No Drawings

METHOD FOR PREPARATION OF ORTHOSILICIC ACID TETRAALKYL ESTERS

The object of the present invention is a method for the preparation of orthosilicic acid tetraalkyl esters in which metallic silicon is reacted with alcohols in the presence of the alkali alcoholates corresponding to the alcohols. The method makes it possible to increase the reaction rates of the known methods and to obtain higher yields, based on the silicon used.

It is known to prepare orthosilicic acid tetraalkyl esters in accordance with German Pat. No. 17 93 222 by reacting metallic silicon with an alkanol in the presence of the alcoholate corresponding to the alkanol, the desired orthosilicic acid ester being employed as solvent. This process is well suited for the preparation of silicic acid tetramethyl ester. However, in the preparation of silicic acid tetraethyl ester and higher esters, when silicon has been charged the reaction rate decreases steadily in the course of the reaction without the reactants having reacted completely. This decrease in reaction rate occurs more rapidly than the decrease in the concentration of the components. In the preparation of silicic acid tetraethyl ester, for example, the result of this is that the silicon employed reacts only to the extent of about 40%, with the reaction then stopping, despite an excess of ethanol.

It is further known to carry out the preparation of orthosilicic acid tetraethyl esters and of the higher silicic acid esters in such a way that, in addition to the procedure described in German Pat. No. 17 93 222, the reaction is carried out in the presence of surface-active substances such as wetting and flotation agents and cyclic organic nitrogen-containing bases, and in the presence of compounds containing methoxy groups, such as sodium methylate. (See German applications DOS 25 32 473 and 25 32 476.) However, while this results in an increase in reaction rate, the yield, based on the silicon used, is not substantially increased.

Surprisingly, it has now been found that in the preparation of silicic acid tetraethyl esters and higher esters a substantial increase in reaction rate and also an increase in yield based on the silicon used can be obtained when the reaction is carried out in the presence of ether alcohols or alkanolamines as supplementary catalysts.

The supplementary catalysts are preferably added to the dispersion of the reactants already before the reaction or at the start of the reaction. However, they may also be added at a point in time when the reaction rate has already dropped sharply, in which case the reaction rate then increases to a level considerably above the level which prevailed at the start of the straight ethyl ester reaction.

The ether alcohols and ethanolamines used in accordance with the invention act as cocatalysts for the alkali alcoholates employed as catalysts. The latter are used in proportions of from 2 to 20 wt. %, based on the total amount of the metallic silicon and of the silicic acid ester charged. Their proportion is preferably comprised between 2 to 15 wt. %, based on the silicon/silicic acid ester dispersion. The proportion of the cocatalysts in accordance with the invention is selected so that the molar ratio between them and the alkali alcoholates used is comprised between 0.5:1 and 1:1.

In principle, all alcohols containing alkoxy groups may be employed as ether alcohols. However, the total number of carbon atoms should not exceed eight. Under this definition fall the ether alcohols known as cellosolves, and in particular compounds of the formula $HO-CH_2-CH_2-OR$, where R stands for ethyl or $CH_2-CH_2-O-C_2H_5$. Saturated aliphatic ether alcohols, e.g., alkoxy alkanols, are especially contemplated.

The alkanolamines which may be used include amino alcohols which likewise have up to eight carbon atoms. The hydrogen atoms of the amino group may be replaced in whole or in part by lower alkyl groups, e.g., $C_{1-4}$ alkyl. Examples are: dimethylaminoethanol, diethylaminoethanol, N-methyldiethanolamine, monoisopropanolamine and diisopropanolamine. Particularly well suited are ethanolamines of the formula $(HO-CH_2-CH_2)_n NH_{3-n}$, where n may assume values between 1 and 3.

In principle, the reaction can be carried out as described in German Pat. Nos. 17 68 781 and 17 93 222, the disclosures of which are hereby incorporated herein by reference. However, in principle it is also possible to work without an excess of silicon and to introduce the silicon together with the alcohol only in such amount as will react in unit time. Advantageously an about 50 to 60 wt. % silicon/silicic acid ester suspension which still can readily be piped and stirred is charged.

The reaction may be carried out discontinuously or continuously. The separation of the reaction product from the reaction mixture is preferably effected distillatively. A crude product of a purity of from 85 to 95% is then obtained which can readily be purified by fractionated distillation. When the method in accordance with the invention is employed, the crude product obtained after distillation does not contain mixed esters which might be formed in a possible side reaction between the silicon used and the cocatalyst, or by transesterification of the introduced silicic acid ester with the cocatalyst.

As is known, in the reaction of silicon and alcohols, hydrogen is formed in the nascent state and to some extent hydrogenates the alcohol present to alkanes and water. (See Houben-Weyl VI/2, page 100.) This water reacts with the catalyst, whose activity then diminishes, and also with the silicic acid ester formed in the alkaline reaction solution. The water may be eliminated by partial distillation of the reaction mixture. The hydrogen gas which forms, or an inert gas such as nitrogen which is also passed through the reaction vessel, may then serve as entrainer.

The water-containing, gaseous distillation products are then so condensed that the condensate cannot flow directly back into the reaction vessel. The distillate drawn off is then returned to the reaction vessel, if this is desired, through appropriate dehydrating means.

The concentration of the various components in the system may be varied over a wide range. However, it will be advantageous to select the conditions so that a mixture which can readily be stirred is present and that the ethylate is present in the alcohol in dissolved form. The replenishment of the catalyst, which as pointed out undergoes some slight consumption during the reaction, may be effected together with the addition of the alcohol.

Pure silicon as well as ferrosilicon or other silicon alloys having a silicon content of over 50% may be employed as metallic silicon. The particle size of the silicon or silicon alloys should not exceed 20μ and to the extent of 90% should be comprised between 2 and 10μ.

In order to more fully illustrate the nature of the invention and the manner of practicing the same, the following examples are presented:

COMPARATIVE EXAMPLE 1

750 g of a 55 wt. % silicon/silicic acid tetraethyl ester suspension (highest-purity silicon with from 99.8 to 100 wt. % Si, particle size $<10\mu$) and 80 g sodium ethylate ($\cong 10.7$ wt. %, based on the suspension used) were introduced into a 2-liter agitator tank with a close-fitting propeller, an inlet pipe, an insulated fractionating column and an internal thermometer and heated to between 145° and 150° C.

Ethanol was then introduced through a rotameter without further heat input in such a way that with maximum ethanol feed a sump temperature of between 140° and 155° C. was maintained in the reactor.

After the reaction vessel had been filled, crude product was withdrawn in order to maintain the liquid level in the reactor.

On the basis of $H_2$ evolution, with an initial ethanol feed rate of 220 ml/h the reaction set in with $H_2$ evolving at the rate of 40 l/h. The ethanol feed rate was gradually reduced to less than 100 ml/h, and after 13 h of operation only 10 l $H_2$/h was measured and the reaction was discontinued.

After further addition of sodium ethylate and heating to reaction temperature, the reaction did not set in again as the ethanol feed was resumed. The crude ester withdrawn, totaling 2118 g, was found to have an Si-$(OC_2H_5)_4$ content of 92%. The average space-time yield was 62 g/l/h and the yield, based on the silicon used, was 52.6% of theory.

EXAMPLE 2

The same procedure was employed as in Example 1. Used were 600 g of a 54 wt. % silicon/Si$(OC_2H_5)_4$ suspension with addition of 75 g sodium ethylate (12.5%, based on the suspension) and 95 g ethyl glycol. (Molar ratio of catalyst to cocatalyst, 1:0.95.)

The particle-size range of the silicon used was the same as in Example 1.

While the reaction temperature was maintained between 140° and 155° C., $C_2H_5OH$ could initially be introduced at the rate of 750 ml/h, with $H_2$ evolving at the rate of 144 l/h. This corresponds at a 360% increase in the reaction rate over that of Example 1.

After the reaction vessel had been filled, the crude ester was withdrawn at the same rate as ethanol was introduced, and the liquid level therefore remained constant. In the course of the reaction, the ethanol feed had to be gradually reduced as in Example 1 in order to maintain the reaction temperature.

At an ethanol feed rate of 90 ml/h and a rate of $H_2$ evolution of 7 l/h, the introduction of ethanol was stopped after 6 h of operation, the crude ester was distilled off, and a further 600 g of silicon/Si$(OC_2H_5)_4$ suspension was added. The reaction resumed as above with respect to ethanol feed, reaction temperature and $H_2$ evolution without further addition of catalyst, and the reaction proceeded accordingly.

After a total of 12 h of operation, 4274 g of crude ester with an Si$(OC_2H_5)_4$ content of 92% was obtained from both charges, which after subtraction of the silicic acid ester used corresponds, at an average space-time yield of 141 g/l/h, to an Si$(OC_2H_5)_4$ yield of 70.2% of theory, based on the silicon used.

EXAMPLE 3

The same procedure was employed as in Example 2, except that ethanolamine was used as cocatalyst in place of ethyl glycol. The reaction charge was 324 g of silicon (particle-size range as in Examples 1 and 2), which was introduced into 276 g of Si$(OC_2H_5)_4$ in the reaction vessel. This corresponds to 600 g of a 54 wt. % silicon/Si$(OC_2H_5)_4$ suspension. After the addition of 75 g of sodium ethylate (12.5%, based on the suspension) and 50 g of ethanolamine (molar ratio of catalyst to cocatalyst, 1:0.74), ethanol could initially be introduced at the rate of 680 ml/h at a sump temperature of 145° C., with hydrogen evolving at the rate of 126 l/h. After 6 h of operation, the reaction rate, determined on the basis of $H_2$ evolution with an ethanol feed of 90 ml/h, had dropped to 10 l $H_2$/h.

The ethanol feed was stopped, crude ester was distilled off, and the reaction continued after the addition of a further 600 g of a 54% silicon/Si$(OC_2H_5)_4$ suspension without the addition of more catalyst. With respect to ethanol feed and hydrogen evolution, the reaction proceeded as above.

A total of 4194 g of crude product with an Si-$(OC_2H_5)_4$ content of 94.8% was obtained from both charges. After subtraction of the silicic acid ester used, this corresponds to a yield of 3424 g of pure product, an average space-time yield of 143 g/l/h, and a yield of 71.1% of theory, based on the silicon used.

EXAMPLE 4

The same procedure was employed as in Example 3. The reaction was carried out on the semi-industrial scale in an agitator of 2 m³ capacity, 825 kg of a 60% silicon/Si$(OC_2H_5)_4$ suspension (=495 kg of silicon, particle size $<10\mu$) being used.

After 45 kg of sodium ethylate (5.5%, based on the suspension) and 30 kg of ethanolamine (molar ratio of catalyst to cocatalyst, 1:0.74) had been added and the introduced suspension had been heated to 145° C., the reaction set in without further heat input upon the addition of $C_2H_5OH$ at the initial rate of 230 l/h.

During the reaction, crude product was withdrawn continuously in order to maintain the liquid level in the reactor. After 32 h of operation, the reaction rate had decreased to the point where $C_2H_5OH$ could be added only at the rate of 30 l/h at a reaction temperature between 145° and 150° C.

The ethanol feed was then stopped and the crude product distilled off quantitatively.

The yield of 93.3% crude ester was 3643 kg. After subtraction of the silicic acid ester used, this corresponds to 3068 kg of pure product. At an average rate of Si$(OC_2H_5)_4$ formation of 96 kg/h, a yield of 83.4% of theory, based on the silicon used, was thus obtained.

What is claimed is:

1. In a method for the preparation of an orthosilicic acid tetraalkyl ester whose ester component contains 2 to 6 carbon atoms by contacting metallic silicon with alcohol in the presence of at least 70 percent of the desired orthosilicic acid tetraalkyl ester and in the presence of an alkali alcoholate corresponding to the alcohol employed, the improvement which comprises carrying out the reaction in the co-presence of an ether alcohol or an alkanolamine.

2. A method according to claim 1 wherein the reaction is carried out in the co-presence of an ether alcohol.

3. A method according to claim 1 wherein the reaction is carried out in the co-presence of an alkanolamine.

4. A method according to claim 2 wherein the ether alcohol is one of the formula $HO-CH_2-CH_2-OR$ wherein R is ethyl or $-CH_2-CH_2-O-C_2H_5$.

5. A method according to claim 3 wherein the alkanolamine has the formula $(HO-CH_2-CH_2)_n NH_{3-n}$ where n has a value between 1 and 3.

6. A method according to claim 1 wherein the molar ratio of alkali alcoholate to ether alcohol or alkanolamine is between 1:0.5 and 1:1.